US011432901B2

(12) United States Patent
Lee et al.

(10) Patent No.: US 11,432,901 B2
(45) Date of Patent: Sep. 6, 2022

(54) SPRING ARM FOR LASER TREATMENT APPARATUS AND LASER TREATMENT APPARATUS INCLUDING SAME

(71) Applicant: LUTRONIC CORPORATION, Goyang (KR)

(72) Inventors: Hee Chul Lee, Goyang (KR); Hyun Woong Yoon, Goyang (KR); Jong Oe Bae, Seoul (KR)

(73) Assignee: LUTRONIC CORPORATION, Goyang (KR)

( * ) Notice: Subject to any disclaimer, the term of this patent is extended or adjusted under 35 U.S.C. 154(b) by 136 days.

(21) Appl. No.: 16/622,242

(22) PCT Filed: Jun. 12, 2018

(86) PCT No.: PCT/KR2018/006650
§ 371 (c)(1),
(2) Date: Dec. 12, 2019

(87) PCT Pub. No.: WO2018/230937
PCT Pub. Date: Dec. 20, 2018

(65) Prior Publication Data
US 2020/0100861 A1   Apr. 2, 2020

(30) Foreign Application Priority Data
Jun. 13, 2017   (KR) .................. 10-2017-0074248

(51) Int. Cl.
*A61B 18/20* (2006.01)
*A61B 90/50* (2016.01)
(Continued)

(52) U.S. Cl.
CPC ............ *A61B 90/50* (2016.02); *A61B 18/203* (2013.01); *A61B 2018/00452* (2013.01);
(Continued)

(58) Field of Classification Search
CPC .................................................... A61C 1/0046
See application file for complete search history.

(56) References Cited

U.S. PATENT DOCUMENTS 4,697,590 A  *  10/1987  Nakai .................. A61B 18/203
                                                            362/401
2003/0028181 A1 *  2/2003  Enomoto ............. A61B 18/201
                                                            606/19
(Continued)

FOREIGN PATENT DOCUMENTS

CN   105288865 A    2/2016
CN   205796264 U   12/2016
(Continued)

OTHER PUBLICATIONS

International Search Report dated Sep. 20, 2018 for International application No. PCT/KR2018/006650.

*Primary Examiner* — Lynsey C Eiseman

(57) ABSTRACT

The present invention relates to a spring arm and a laser treatment apparatus including same and, particularly, to a spring arm for a laser treatment apparatus, which can provide an appropriate support force according to a change in the center of gravity of a link at an initial high rotation angle and at a low rotation angle during use, and a laser treatment apparatus including same. According to the present invention, a user fatigue degree can be reduced and accuracy of the apparatus when in use can be improved.

13 Claims, 16 Drawing Sheets

(51) Int. Cl.

| | |
|---|---|
| A61B 18/00 | (2006.01) |
| A61C 1/00 | (2006.01) |
| A61F 9/008 | (2006.01) |
| A61N 5/067 | (2006.01) |
| B25J 1/12 | (2006.01) |

(52) U.S. Cl.
CPC ....... *A61B 2018/207* (2013.01); *A61C 1/0046* (2013.01); *A61F 9/008* (2013.01); *A61N 5/067* (2021.08); *B25J 1/12* (2013.01)

(56) References Cited

U.S. PATENT DOCUMENTS

| | | | |
|---|---|---|---|
| 2008/0033410 A1* | 2/2008 | Rastegar | A61B 18/20 606/9 |
| 2009/0187176 A1* | 7/2009 | Assa | A61B 18/201 606/17 |
| 2009/0227830 A1 | 9/2009 | Pillutla et al. | |
| 2014/0324033 A1 | 10/2014 | Goo | |
| 2017/0119413 A1* | 5/2017 | Romo | A61B 1/00045 |

FOREIGN PATENT DOCUMENTS

| | | |
|---|---|---|
| JP | 5453325 B2 | 3/2014 |
| KR | 20130057690 A | 6/2013 |
| KR | 20170056058 A | 5/2017 |
| WO | WO2017080016 A1 | 5/2017 |

\* cited by examiner

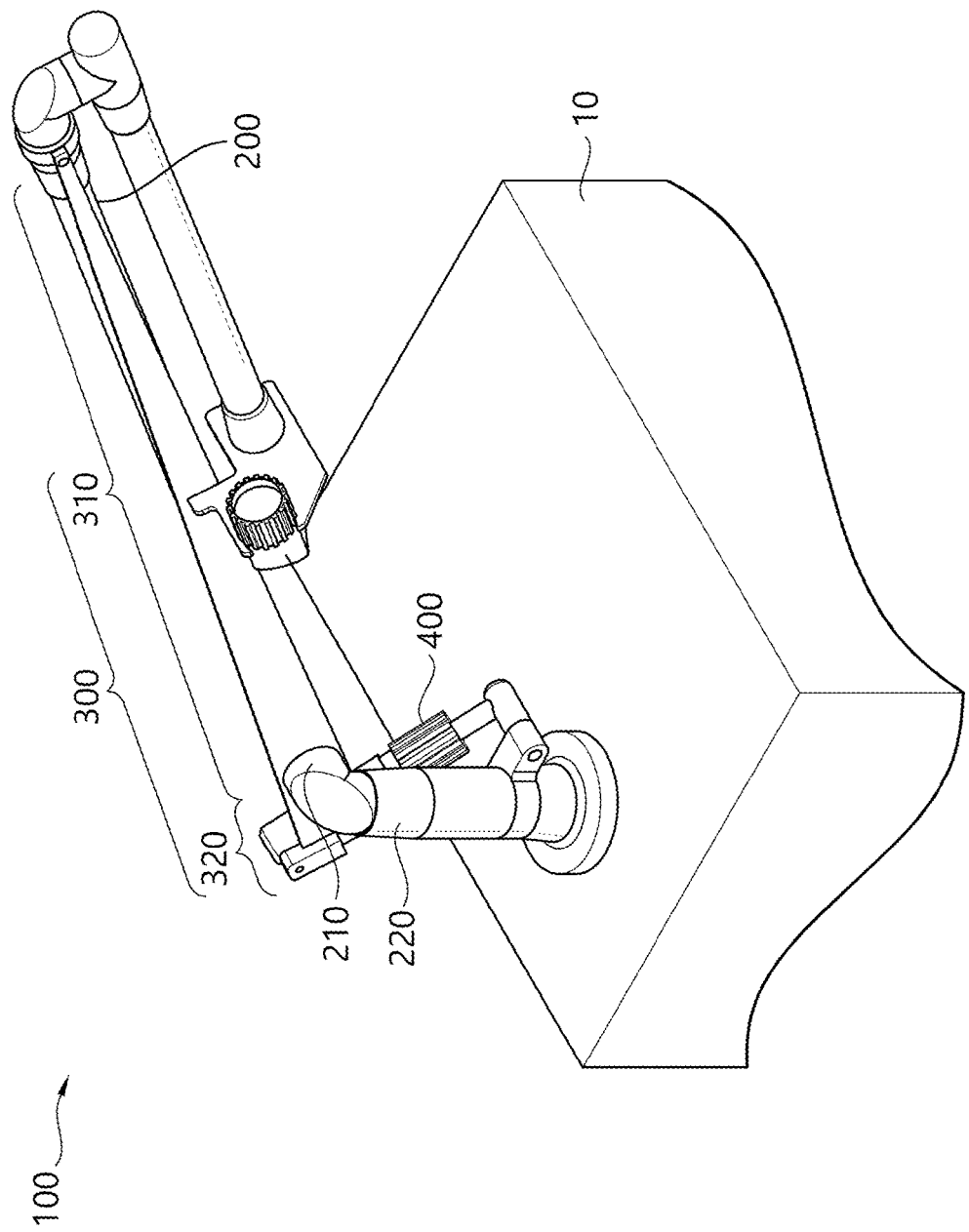

SPRING ARM FOR LASER TREATMENT APPARATUS AND LASER TREATMENT APPARATUS INCLUDING SAME

This application is a national stage application, filed under 35 U.S.C. § 371, of International Patent Application No. PCT/KR2018/006650, filed on Jun. 12, 2018, which claims the priority of Korean application No. 10-2017-0074248, filed on Jun. 13, 2017, the contents of which are incorporated by reference.

TECHNICAL FIELD

The present invention relates to a spring arm for a laser treatment apparatus and a laser treatment apparatus including the same, and more specifically, a spring arm in which a hand piece that a user uses by grabbing is connected to at one end thereof and a laser treatment apparatus including the same.

BACKGROUND ART

Recently, treatment techniques using a laser are widely used. Such treatment apparatus using a laser are used in ophthalmology, dentistry, surgical operations, dermatology, etc.

In general, laser treatment apparatus used for lesions, such as skin diseases or vascular diseases occurring on the skin, achieve the therapeutic purpose by irradiating the skin with a laser having a constant wavelength and intensity.

In particular, it takes a significantly long time for a user to grab a laser treatment apparatus and maintain in the grabbed state for treatment in a position adjacent to a lesion area, and it is necessary that the user be able to support the laser treatment apparatus with an appropriate force according to the use angle for the user fatigue degree and accuracy of surgery.

However, in the prior art, there was a problem in that a counter weight was provided on the opposite side of a hand piece with respect to a mast being supported, but the counter weight was not able to provide an appropriate support force according to the rotation angle of the arm. FIG. 1 shows torque values according to the angles when the counter weight was applied. As shown, the counter weight rotates together when the arm rotates so that a support force is determined mechanically, and at the early stage of use, there was a limitation in that it was difficult to reduce the difference between the force required to move from a high angle to a low angle during the initial use and the force required during use at a low angle.

DISCLOSURE

Technical Problem

Objects of the present invention are to provide a spring arm for a laser treatment apparatus to solve the above-mentioned problem that the arm of the laser treatment apparatus does not provide an appropriate support force, and a laser treatment apparatus including the same.

Technical Solution

As a solution to the above problem, it is possible to provide a spring arm for a laser treatment apparatus, which includes: a mast, in which one end is mounted on the main body and a path for laser movement is formed inside thereof; an arm connected to the other end of the mast and a path for laser movement is formed inside thereof, and is configured to rotate in a vertical direction around a connecting part connected to the mast; a support link including an arm supporting part that rotates around the connecting part and is configured to support the arm at one side around the connecting part; and an elastic part supporting part extended to a predetermined length on the other side; and an elastic part, in which one side is connected to a point of the elastic part supporting part, and the other side is connected to the mast, so as to allow the arm to transmit a different support force to the arm depending on the vertical rotation.

In particular, the elastic part may be configured to include a first hinge part connected to a point of an elastic part supporting part and a second hinge part connected to a point spaced a predetermined distance from the central axis of the mast.

In addition, the second hinge part may be connected to a point which is spaced a predetermined distance from the central axis of the mast to a direction where the arm is extended.

In addition, in the elastic part is configured to positioning the arm at the maximum high angle without external force applied to the spring arm, and is configured to transmit a support force even when the arm is positioned at the maximum high angle.

Furthermore, the elastic part may be configured such that the amount of change in a support force according to the angle gradually decrease as the arm rotates from the maximum high angle to the minimum low angle.

In addition, the elastic part may include: a housing; a rod, which is inserted from one side of the housing; and a spring, which is provided inside the housing so as to transmit an elastic force between the housing and the rod.

Meanwhile, the spring may disposed between a flange provided inside the housing in the rod, and a surface formed an opening into which the rod is inserted, and thereby supported to be compressed when the rod is extended.

In addition, the elastic part may be configured to further include an elasticity adjusting part for adjusting the distance between the inner surfaces of both sides of the housing so as to adjust the restoring force of the spring.

Meanwhile, the point to which the first hinge part is connected may be a point in the elastic part supporting part that is spaced apart from a straight line connecting the arm supporting part and a connecting part thereof.

Meanwhile, the support link may be formed in a straight line and may be configured to further include a first hinge part fastening part that is configured to be connected to a point spaced a predetermined distance from the straight line.

In addition, the elastic part may be configured to have a length that is able to constrain the rotation angle of the arm supporting part at a degree of 0 to 90 based on the horizon.

Meanwhile, the mast may be formed extending in a height direction, in which the arm, the support link, and the elastic part may be configured to rotate together based on the central axis of the mast.

Furthermore, the mast may be connected to a connecting part of an arm that is formed to have a predetermined length on a side, and the support link may be provided with a connecting part hole for insertion of the connecting part.

Meanwhile, the first hinge part may be connected to a first connecting area within a predetermined angle and a predetermined distance based on the extended axis of the arm supporting part.

In addition, the second hinge part may be connected to a second connecting area within a predetermined distance in a direction opposite to the first hinge part from the axis of the mast.

In particular, the elastic part may be determined with regard to its minimum length so as to limit the high angle of the arm supporting part.

In addition, it is possible to provide a laser treatment apparatus, which includes: a main body, which is configured including a laser oscillating part; a hand piece, which is configured to allow a user to grab and irradiate a laser onto a lesion area; and a spring arm 100, in which one end is mounted on the main body and the other side is connected to the hand piece to form a path for laser movement, wherein the spring arm 100 includes: a mast, in which the one end is mounted on the main body and a path for laser movement is formed inside thereof; an arm, which is connected to the other end of the mast and a path for laser movement is formed inside thereof, and is configured to rotate in a vertical direction around a connecting part connected to the mast; a support link, which comprises an arm supporting part that rotates around the connecting part and is configured to support the arm at one side around the connecting part; and an elastic part supporting part that is extended to a predetermined length on the other side; and an elastic part, in which one side is connected to a point of the elastic part supporting part, and the other side is connected to the mast, so as to allow the arm to transmit a different support force to the arm depending on the rotation angle in the vertical direction.

Advantageous Effects

The spring arm for a laser treatment apparatus according to the present invention and a laser treatment apparatus including the same can provide an appropriate support force according to a change in the center of gravity of a link at an initial high rotation angle and at a low rotation angle during use, and thus have the effects of reducing user fatigue degree and improving accuracy of the apparatus when in use.

DESCRIPTION OF DRAWINGS

FIG. 2 is a perspective view of the spring arm of a laser treatment apparatus according to the present invention.

MODE FOR INVENTION

Figure 1:
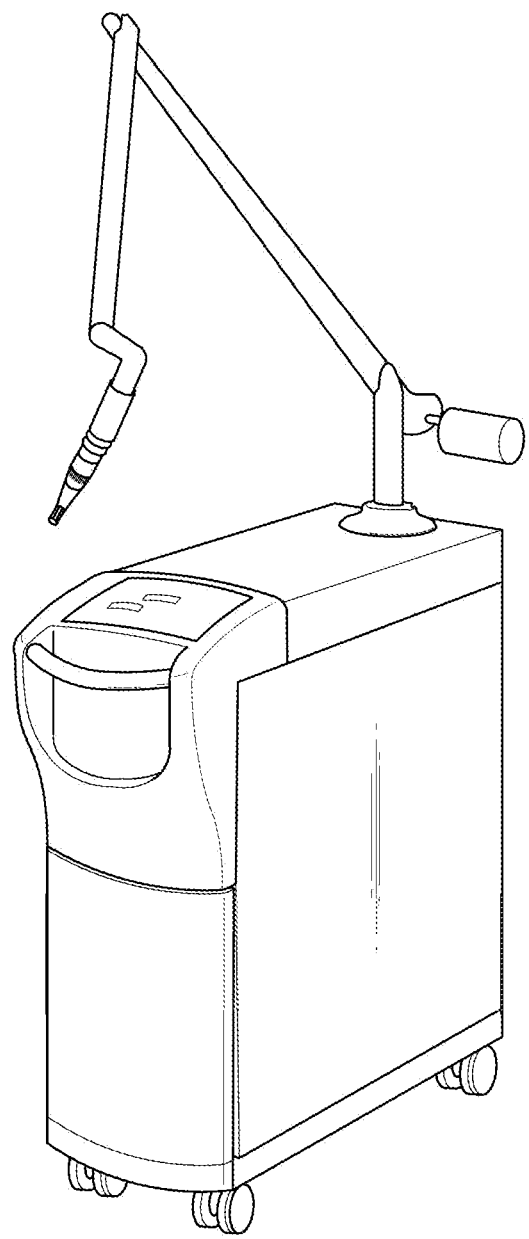
FIG. 1 is a view illustrating a torque value according to the arm and angle of a conventional laser treatment apparatus.

Hereinafter, the spring arm for a laser treatment apparatus according to an embodiment of the present invention and a laser treatment apparatus including the same will be described in detail with reference to the accompanying drawings. In addition, in the description of the following embodiments, the names of each component may be referred to by other names in the art. However, if functional similarities and identities are present they can be regarded as equivalent configurations, even if modified embodiments are adopted therein. In addition, the symbols added to each component is described for convenience of description. However, the contents shown in the drawings in which these symbols are described do not limit each component to the ranges in the drawings. Similarly, even if an embodiment in which the configuration on the drawings is partially modified is adopted, it can be regarded as an equivalent configuration if there is functional similarity and identity. In addition, in view of the general level of those skilled in the art, if it is recognized as a component to be included naturally, the description thereof will be omitted.

Figure 3A:
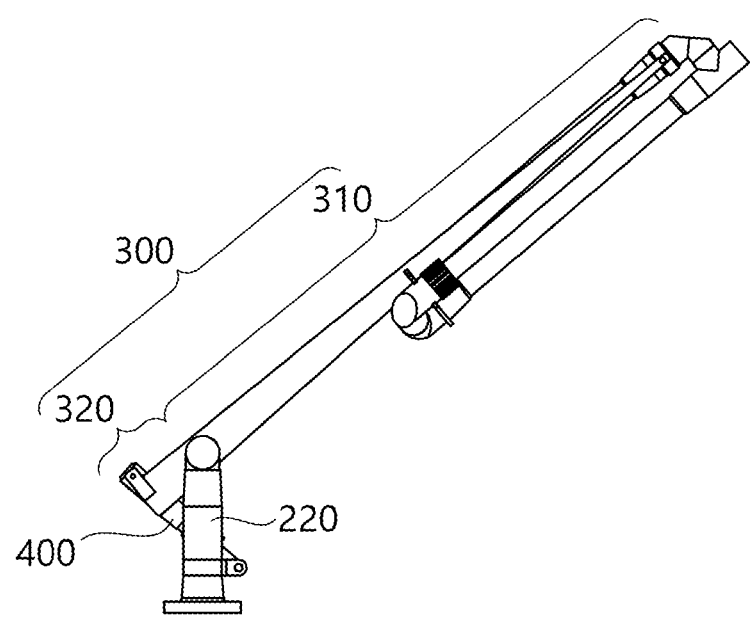
FIGS. 3A and 3B are front and side views of the spring arm according to the present invention.
Figure 3B:
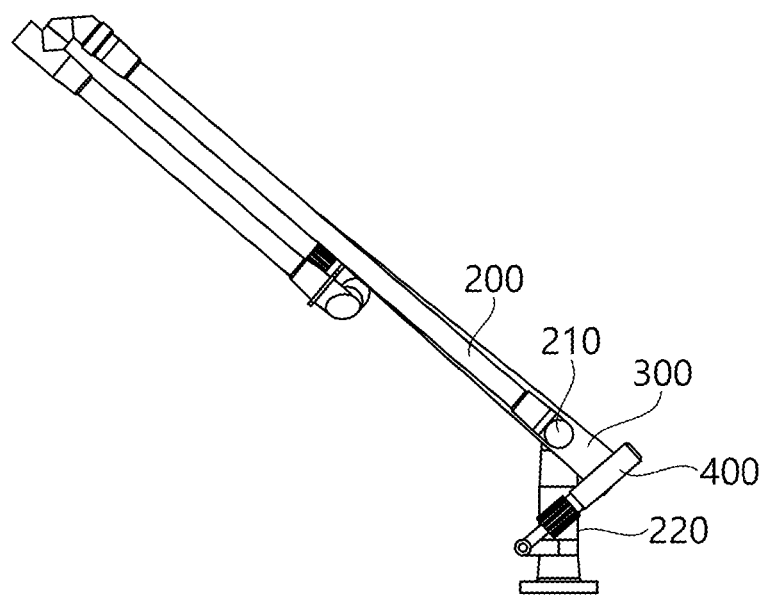
Figure 4:
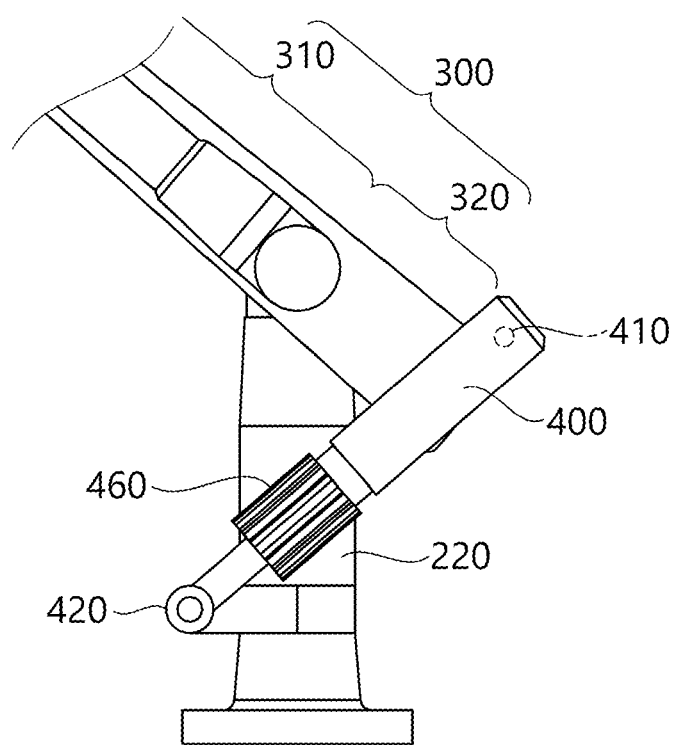
FIG. 4 is an enlarged perspective view of the elastic part.
Figure 5:
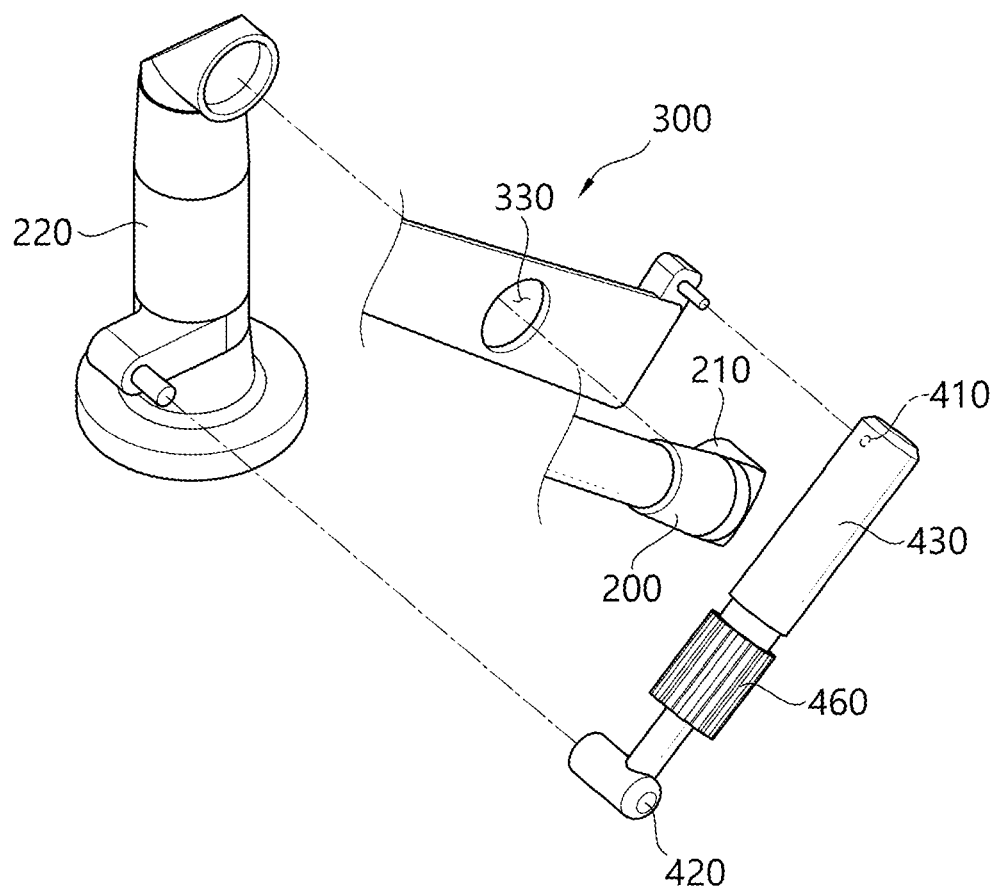
FIG. 5 is an exploded perspective view of the spring arm.
Figure 6:
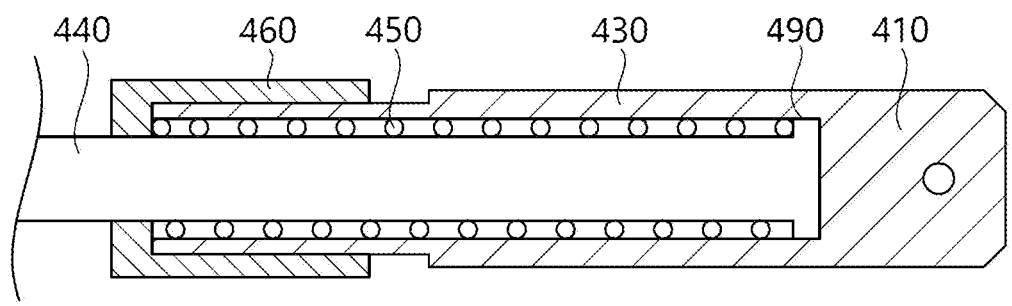
FIG. 6 is a cross-sectional view of the elastic part.

FIG. 2 is a perspective view of the spring arm of a laser treatment apparatus according to the present invention; FIGS. 3A and 3B are front and side views of the spring arm 100 according to the present invention; FIG. 4 is an enlarged perspective view of the elastic part; FIG. 5 is an exploded perspective view of the spring arm 100; and FIG. 6 is a cross-sectional view of the elastic part 400.

As illustrated, the laser treatment apparatus according to the present invention may include a main body 10, a spring arm 100, and a hand piece.

The main body 10 accommodates a laser oscillating part (not shown) that oscillates a therapeutic laser that is irradiated to a lesion of the skin. In particular, although not shown inside the main body 10, an input part, a driving part, a controlling part, etc. are accommodated.

The hand piece (not shown, see FIG. 1) is connected to one side of the spring arm 100 and is grabbed by an operator and moved to the skin of a patient in need of irradiation of the therapeutic laser. The hand piece then irradiates the patient's skin with a therapeutic laser provided from a laser oscillating part of the main body 10.

The hand piece is held by the operator so that the therapeutic laser oscillated in the laser oscillating part is incident through the arm and the incident therapeutic laser is irradiated to a subject for operation such as skin. The hand piece may be configured to include a wavelength converting means for converting and outputting the therapeutic laser of a first wavelength from the laser oscillating part to the therapeutic laser of a second wavelength (not shown); and a filter for transmitting only the light of the second wavelength among the therapeutic lasers output from the wavelength converting means (not shown), The laser oscillating part of the main body 10, which provides a therapeutic laser for the hand piece, is characterized in that it consists of a medical Q-switching Nd: YAG laser that oscillates in the wavelength of 1,064 nm, and the second wavelength is in the wavelength of 2,700 nm to 3,000 nm (more preferably 2,936 nm). The laser oscillating part used as the medical Q-switching Nd: YAG laser is already known before the filing of the present application and the detailed description thereof is omitted herein.

The spring arm 100 interconnects the main body 10 and the hand piece. The spring arm 100 may be configured to include a plurality of links so that the position of the hand piece can be adjusted by the operator holding the hand piece. In addition, the spring arm 100 may be configured to include a path for laser movement, Which becomes a path for delivering the laser generated from the main body 10 to the hand piece. The spring arm 100 is configured to support the hand piece with an appropriate force when the user changes its position by holding the hand piece. The user can use the hand piece located at one point and move it to the next position, the spring arm 100 supports the hand piece with an appropriate force during fixation or movement, thereby reducing user fatigue and helping to precisely change the position.

The spring arm 100 may be configured to include a plurality of links to enable the rotation up and down and left and right, and may be configured to have a minimum of three degrees of freedom. The spring arm 100 may be configured to be positioned at the highest angle when the hand piece is not in use, and at low angles when in use, for placement efficiency.

The spring arm 100 may be configured to include a mast 220, an arm 200, a support link 300, and an elastic part 400.

The mast 220 may be configured to mount the spring arm 100 on the main body 10 described above. The mast 220 is configured to extend a predetermined length in the height direction, and a hollow is formed inside the mast 220 thereof to become a path for the laser movement. The mast 220 may be configured so that the arm 200, the arm supporting part 310, and the elastic part 400, which are connected to the mast 220 with respect to the central axis in the height direction, can pivot at a predetermined angle. In addition, the mast 220 is configured so that the elastic part 400 can be connected at a predetermined distance from the central axis of the mast 220.

The arm 200 may be connected to the mast 220, in which a hollow to form a path for the laser to move may be formed inside thereof and the hollow may be formed extending in the longitudinal direction. The arm 200 may be configured in plurality to deliver a laser to a long distance and the end of the arm 200 may be connected to the above-described hand piece. The arm 200 is connected to the mast 220 after extending a predetermined distance in the rotational axis direction so that the laser can continuously pass through even if the arm 200 rotates up and down. That is, two perpendicular paths are formed when entering the arm 200 from the mast 220. The arm 200 may be connected to the mast 220 by forming a connecting part 210 at the center of rotation at the time of a vertical rotation, in which the connecting part 210 is connected on a side of the mast 220 so that the laser can pass through.

A support link 300 is configured to support the arm 200 when the arm 200 moves in a vertical direction around the connecting part 210. In particular, on the arm 200, a force to be inclined to a low angle according to its own weight and a force pulled by the user from the outside become to act simultaneously, and here, the arm 200 is configured to transmit the force generated in the opposite direction to arm 200.

The support link 300 is formed to extend in a longitudinal direction and may be configured to rotate in a vertical direction with the arm 200 around the connecting part 210. A connecting part hole 330 is formed in the support link 300 into which the connecting part 210 is inserted, and is fixed with the arm 200 in a state where the connecting part 210 of the arm 200 is inserted into the connecting part hole 330.

The support link may be configured to include the elastic part supporting part 320, which is provided on the opposite side with respect to the arm supporting part 310 that supports the arm 200, based on the connecting part hole 330. The arm supporting part 310 may be configured to be connected to the arm 200 at a plurality of points so as to stably support the arm 200. The elastic part supporting part 320 is hinged to an elastic part 400 to be described later, and is configured to receive a support force generated from the elastic part 400. The arm supporting part 310 may be configured in a shape somewhat longer than the elastic part supporting part 320, and the arm supporting part 310 and the elastic part supporting part 320 may be configured to be formed at a predetermined angle based on the connecting part hole 330. Specifically, in the elastic part supporting part 320, the point where the first hinge part 410 is to be connected to the elastic part 400 to be described later may be formed to be spaced apart at a predetermined angle with respect to the connecting part hole 330. That is, the first hinge part 410 may be provided to be spaced apart from a straight line that connects the arm supporting part 310 and the connecting part 210 groove.

The elastic part 400 is configured such that the structure including a hand piece and arm 200 can offset the torque acting on the arm supporting part 310 by gravity and a force generated by the user. The elastic part 400 may be configured to include the first hinge part 410, which is connected to the elastic part supporting part 320 of a support link, and a second hinge part 420, which is connected to a side of the mast 220. The elastic part 400 is configured to provide a support force even when the arm 200 is in a position with the highest angle, and is configured to support a different support force according to the angle rotation of the arm 200. Meanwhile, the position for connecting the support force and the hinge part will be described in detail later.

The elastic part 400 may be configured to include a housing 430, a rod 440, a flange 490, a spring 450, a first hinge part 410 and a second hinge part 420, and an elasticity adjusting part 460. The housing 430 forms a space in which the spring 450 is accommodated and the first hinge part 410 is provided on a surface of the outside. The rod 440 performs a linear movement in a state where one side is inserted inside the housing 430, and the second hinge part 420 on the side of the mast 220 is provided on the other side. One end of the rod 440 located inside the housing 430 is provided with a flange 490. The spring 450 may be configured to be provided between the flange 490 and one surface, in which an opening into which the rod 440 in the housing 430 is inserted is formed, and the spring 450 may be compressed to generate a restoring force as the distance between the first hinge part 410 and the second hinge part 420 increases. The elasticity adjusting part 460 is configured to be able to adjust the distance between one side, where an opening into which the rod 440 is inserted is formed, and the other side. Therefore, the maximum extension length of the spring 450 is constrained so that the strength of a restoring force over the entire angle can be adjusted.

Hereinafter, the connection region of the hinge part will be described in detail with reference to FIG. 7.

Figure 7:
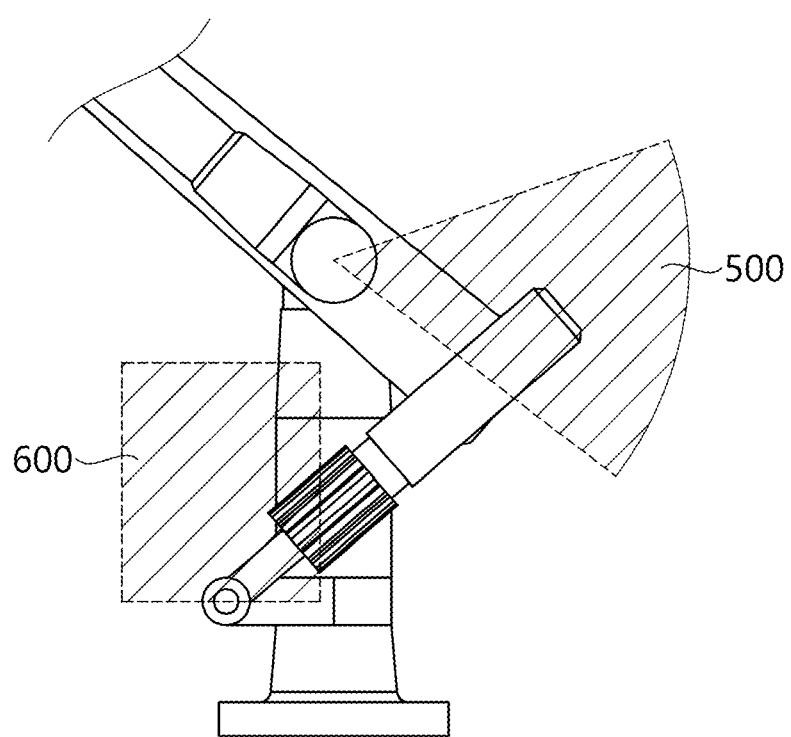
FIG. 7 is a view illustrating a connection region of the elastic part.

FIG. 7 is a view illustrating a connection region of the elastic part 400. As illustrated, the first hinge part 410 of the elastic part 400 may be connected to a first connecting area 500 of the elastic part supporting part 320, and the second hinge part 420 may be connected to a second connecting area 600. The first connecting area 500 may be formed at a predetermined distance and a predetermined angle from the connecting part hole 330 among the regions in a side of the elastic part supporting part 320. In particular, the first connecting area 500 may be determined in an upward side based on a straight line from which the arm supporting part 310 is extended. As the first hinge part 410 moves away from the connecting part hole 330, the torque value by the elastic part 400 increases, and at the same time, the amount of change in torque according to the change in angle increases. The predetermined angle affected by the torque caused by gravity according to the up-and-down rotation angle of the arm 200 varies, at which time a restoring force cycle of the elastic part 400 varies by changing the predetermined angle. In particular, the second connecting area 600 may be determined in a direction where the arm 200 is extended, based on the mast 220.

The second hinge part 420 of an elastic part 400 may be connected to the second connecting area 600, may be spaced in a vertical direction from the center of rotation of the arm 200, and may also be a point spaced a predetermined distance in a horizontal direction. In the second connecting area 600, as the distance in a vertical direction increases, the change in repulsive force due to the rotation of the arm 200 slows down, and the horizontal movement simultaneously affects the amount of change in repulsive force and a restoring force cycle, Meanwhile, since the torque value by gr ay vary according to the specific size, shape, and material of the arm 200, the size of the arm supporting part 310 the size and length of the elastic part supporting part 320, and the length, specific values, and elastic modulus of the elastic part 400 will be omitted herein.

Figure 8:
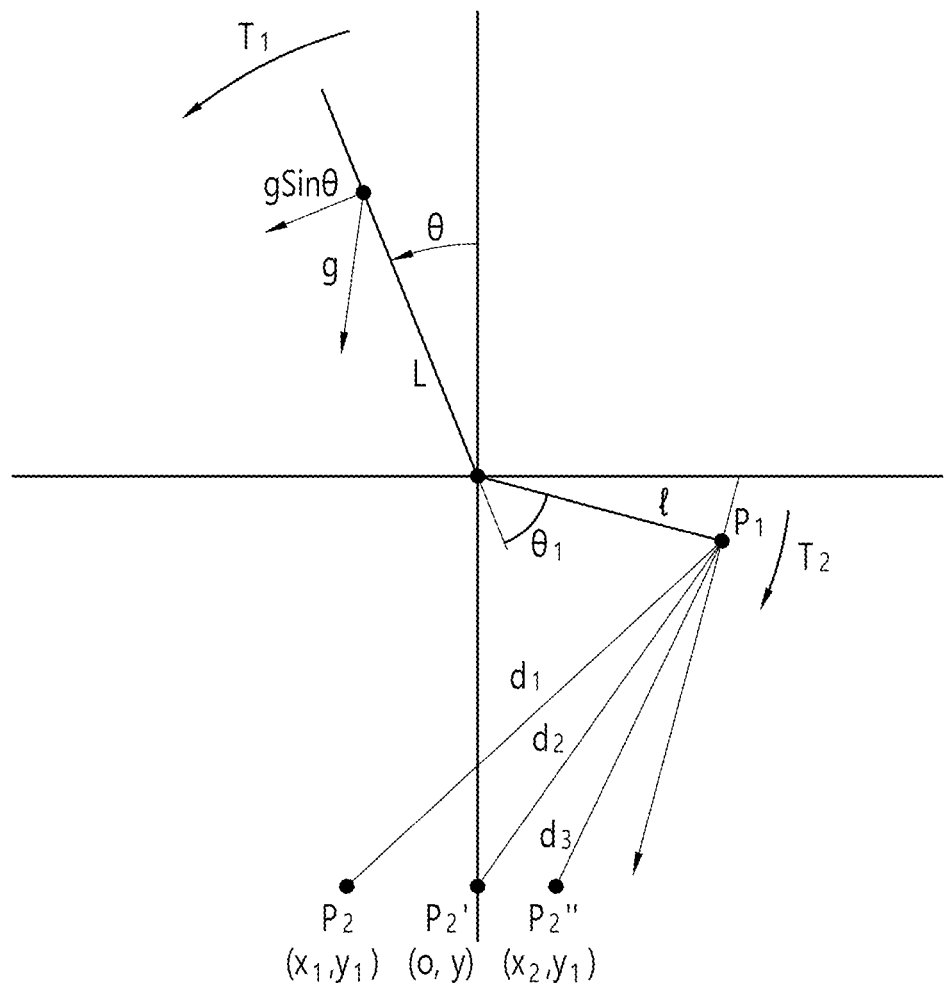
FIG. 8 is a diagram illustrating a relationship between the arm and the elastic part.
Figure 9A:
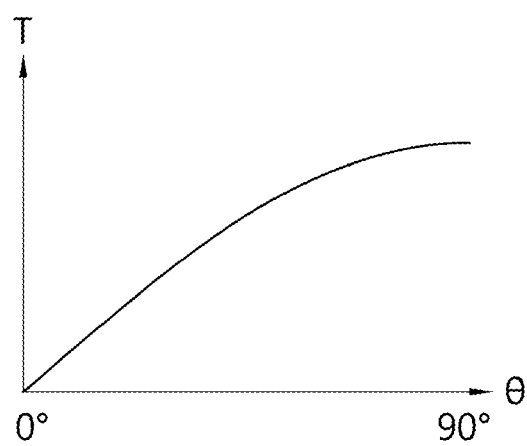
FIGS. 9A, 9B, and 9C are graphs illustrating forces and moments according to angles, respectively.
Figure 9B:
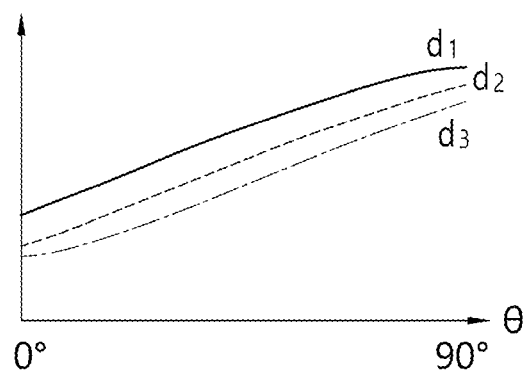
Figure 9C:
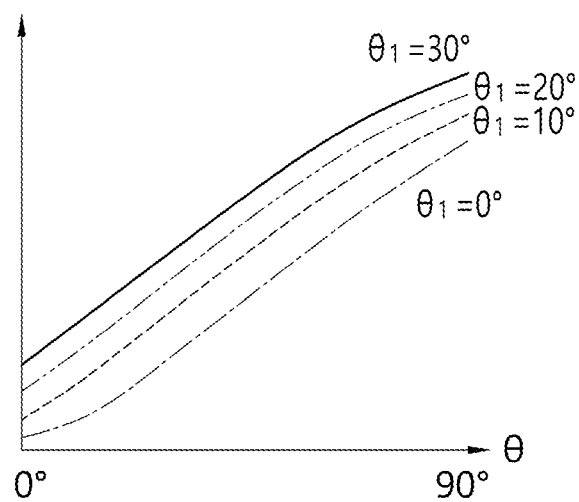

FIG. 8 is a diagram illustrating a relationship between the arm 200 and the elastic part 400, and FIGS. 9A, 9B, and 9C are graphs illustrating forces and moments according to angles, respectively. The arm supporting part 310 is illustrated briefly around the connecting part 210, which is the rotating center, and the connecting points of the first hinge part 410 and the second hinge part 420 are illustrated. Meanwhile, the positions in the first hinge part 410 and the second hinge part 420 will be described based on the rotation center of the hinge part.

T1=a torque action on a side of the arm supporting part 310

T2=a torque action on a side of the elastic part supporting part 320

θ: a rotation angle of the arm 200 from the vertical axis

θ1: a difference in angle between the arm supporting part 310 and the elastic part supporting part 320

L: a linear distance between the center of gravity and the rotation center of the arm 200 l: a distance between the center of the first hinge part 410 and the center of rotation P1 ($x_θ$, $y_θ$): a position for connecting the first hinge part 410

P2, P2', P3": a position for connecting the second hinge part 420 d: a length of the elastic part 400

In particular, the rotation angle of the arm 200 around the connecting part 210 may be in a degree of 90 to 180, and may have an operating angle in a degree of 0 to 90 with respect to the vertical axis. Meanwhile, since the user rotates the arm 200 from the vertical axis to the horizontal axis, explanation will be given in which e angle around the vertical axis is referred to as "initial position" and the peripheral angle of the horizontal axis is referred to as "late position".

The torque generated by gravity acting on the center of gravity of the arm 200 may vary according to the rotation angle of the arm 200. In particular, the center of gravity can be expressed as follows, including all of the weight (M) of the arm 200, a support link, and a hand piece.

$$T1 = MgL \sin θ$$

With regard to the values, as illustrated in FIG. 9A, the size of the arm 200 becomes greater as the arm 200 draws near to the horizontal.

Meanwhile, in the elastic part 400, the restoring force increases linearly as the length of the elastic part 400 increases within the operating range. The effect of increasing the restoring force on the torque varies according to the angle between the elastic part supporting part 320 and the elastic part 400. In particular, since the linear force acts at an angle at which the elastic part 400 is disposed, the force of the component in perpendicular to the elastic part supporting part 320 becomes involved in a torque (T2) that acts on the elastic part supporting part 320, at the first hinge point. Eventually, while the arm 200 is changed from the initial position to the late position, the elastic force is continuously increased according to the increase of the length of the elastic part 400, the component perpendicular to the elastic part supporting part 320 may continue to decrease. Therefore, these values vary according to the connecting positions of the elastic part 400, and they prevent a sudden change in torque during the use by a user, and the connecting position of the elastic part 400 is determined so as to minimize the force required to maintain as the positions for use.

Hereinafter, the influence of the position of the second hinge part 420 will be described with reference to FIG. 9B. In FIG. 9B, the changes in the length of the elastic part 400 according to the angle when l=100, y1=−150, θ1 2.0 degrees, x1=−40, x2=0, and x3=+40 are illustrated.

Meanwhile, the coordinate of the point at which the first hinge part 410 is connected may be defined as follows.

$$P1(l \sin(θ+θ1), -l \cos(θ+θ1))$$

Meanwhile, the position of a second hinge pan 420 may be P2, P2', and P2", where the coordinates are as follows.

$$P2(x1, y1), P2'(x2, y1), P''(x3, y1)$$

In particular, the size of a restoring force which is applied according to the change in the length of each elastic part 400 may vary. When the position of the first hinge part 410 is the same, each distance to the second hinge part 420 is as follows.

$$d1 = (x1 - l \sin(θ+θ1))^2 + (y1 + l \cos(∂4+θ1)^2)^{0.5}$$

$$d2 = (x2 - l \sin(θ+θ1))^2 + (y1 + l \cos(θ+θ1)^2)^{0.5}$$

$$d3 = (x3 - l \sin(θ+θ1))^2 + (y1 + l \cos(θ+θ1)^2)^{0.5}$$

Reviewing the above results, when the second hinge part 420 is arranged in a direction opposite to the first hinge part 410 around the mast 220, the amount of change is large in the initial position and tends to decrease in the late position. In contrast, when the first hinge part 410 and the second hinge part 420 are located in the same direction around the mast 220, the amount of initial change is small and is thus not desirable. Therefore, it is possible to select the amount of change in torque generated initially by appropriately selecting the position of the second hinge part 420. In particular, when there is a sudden change initially in the length of the elastic part 400, the force required to be pulled up by the user rapidly increases, and thus it is preferable to select a position where the amount of change in torque is not significant initially. Referring again to FIG. 9B, when the first hinge part 410 and the second hinge part 420 are selected in different directions around the mast 220, a sudden change in length at the initial position can be prevented.

Hereinafter, the influence of the change in angle between the arm supporting part 310 and the first hinge part 410 when the second hinge part 420 is positioned at P2 will be described, referring to FIG. 9C. As illustrated, when the difference in angle between the arm supporting part 310 and the first hinge part 410 is 0 degrees, 10 degrees, 20 degrees, and 30 degrees, the change in length of the elastic part 400 is illustrated, and the change tends to vary between the initial position and the late position, according to the position of the first hinge part 410, which is in a circular motion. Meanwhile, the position of the first hinge part 410 affects the tangential component that affects the torque in the restoring force occurring in the elastic part 400.

Figure 10A:
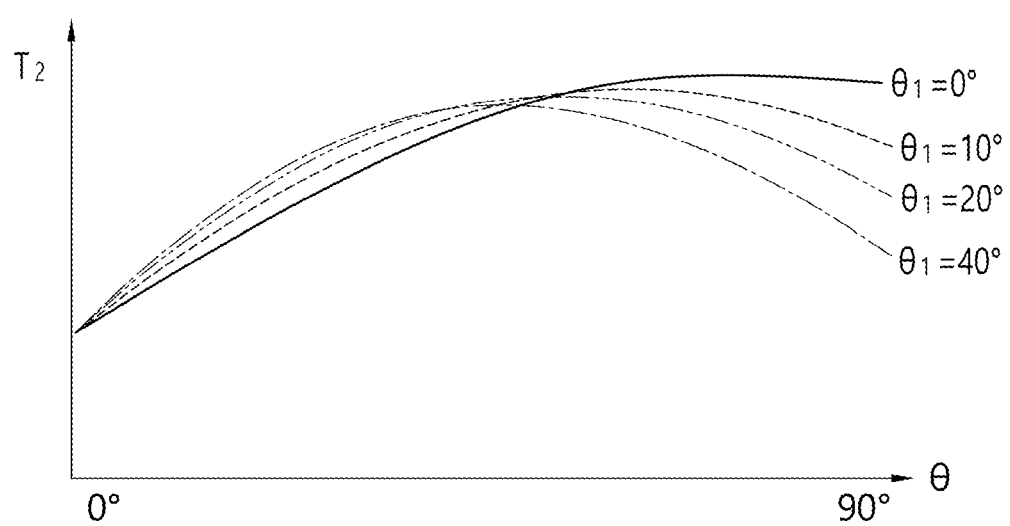
FIGS. 10A and 10B are graphs illustrating torque values by the elastic part.

Hereinafter, the torque values by the elastic part 400 will be described with reference to FIG. 10. FIGS. 10A and 10B are graphs illustrating torque values by the elastic part 400.

The torque generated by the elastic part 400 in the first hinge part 410 varies according to the angle and the values are as follows.

$$T_2 = sd\sin\left(\cos^{-1}\frac{(x_\theta - x)}{d} - (\theta_1 + \theta) + 90w\right)$$

In particular, comparison results of the torque values between the torque value (T1) of the arm 200 and the torque value (T2) according to the angle of the arm supporting part 310 and the first hinge part 410 are as follows.

In particular, the torque according to the elastic part 400 between the angles of the arm 200 in a range of 40 degrees to 60 degrees is shown to be the largest section, and then the torque tends to decrease again. This is because when the angle of the arm 200 increases, the elastic part 400 is continuously stretched by the elastic part supporting part 320, but the component of the force in vertical direction that generates the torque gradually decreases.

Referring to FIG. 10A again, torque (T2) is shown in which the angle (θ1) between the arm supporting part 310 and the elastic part supporting part 320 is 0, 10, 20, and 40 degrees, respectively. As the angle (θ1) between the arm supporting part 310 and the first hinge part 410 increases, the time for reducing the torque value comes earlier. Meanwhile, in comprehensive consideration of the length of the arm 200, the moment of inertia according to the shape of the arm 200, etc. the angles of the arm supporting part 310 and the first hinge part 410 may be selected so that an appropriate support force can be exerted in the elastic part 400.

Figure 10B:
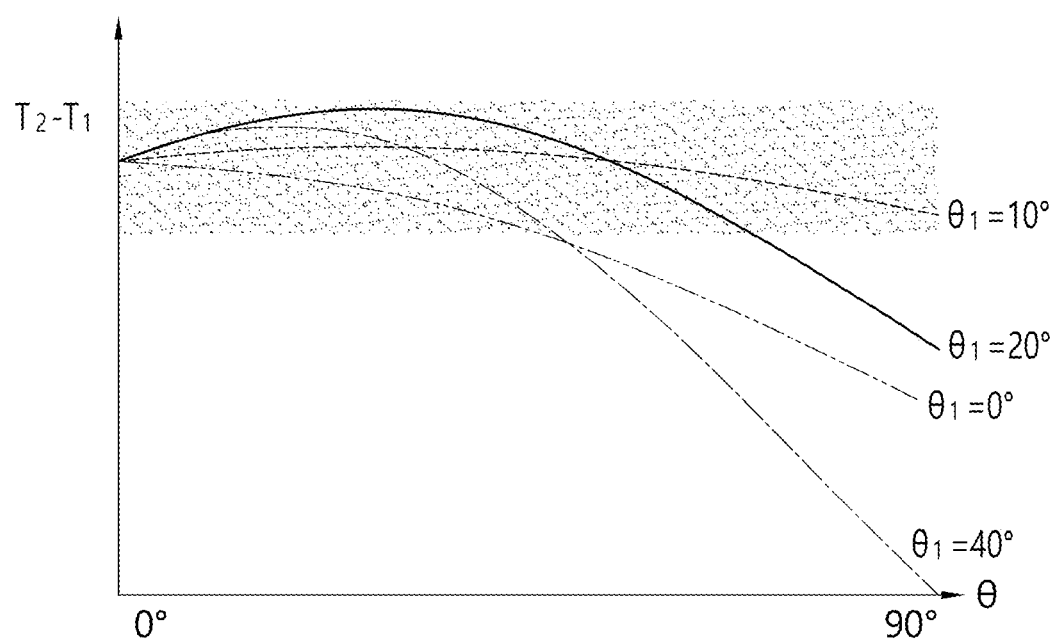

Referring to FIG. 10B, the difference between the torque (T1) by gravity acting on the arm 200 and the torque (T2) by the elastic part 400 is shown. In particular, the difference between the two torques (T2–T1) becomes the force required by the user during operation. A graph with respect to the difference in torque values (T2–T1) is shown after the initial torque (T2) value is set equal by adjusting the spring constant value. From this, it can be seen that as the angle increases, the overall amount in change tends to decrease, but within a predetermined range, the amount in angle change decreases and then the amount in change increases again. Reviewing from the mechanical embodiment described above, it can be seen that the angle (θ1) between the arm supporting part 310 and the first hinge part 410 is limited predetermined range of force required by the user so as to operate the arm 200 in a range of 5 degrees and 15 degrees. However, in the above embodiment, the angle (θ1) between the arm supporting part 310 and the first hinge part 410 may vary somewhat depending on the length of the arm supporting part 310, the length of the elastic part supporting part 320, and the position of the second hinge part.

Meanwhile, the overall difference in torque value (T2–T1) may be adjusted by varying a spring constant while maintaining the trend, and may also be adjusted through an elasticity adjusting part 460. Eventually, the user uses the apparatus by grabbing the hand piece in the late position, and thus, it is desirable to minimize the force required so as to fix the position in the late position.

Meanwhile, the elastic force of the elastic part 400 may vary depending on the characteristics of a spring 450, and thus can be selected with an appropriate strength, and in addition, can also be adjusted by manipulating the elasticity adjusting part 460. Meanwhile, even when a different spring 450 is selected, the trend shown in FIG. 10 can be maintained.

Hereinafter, another embodiment according to the present invention will be described with reference to FIG. 11. This embodiment may also be configured to include the same components as in the above-described embodiments, and the description thereof will be omitted and only differences will be described in order to avoid duplicated descriptions.

Figure 11:
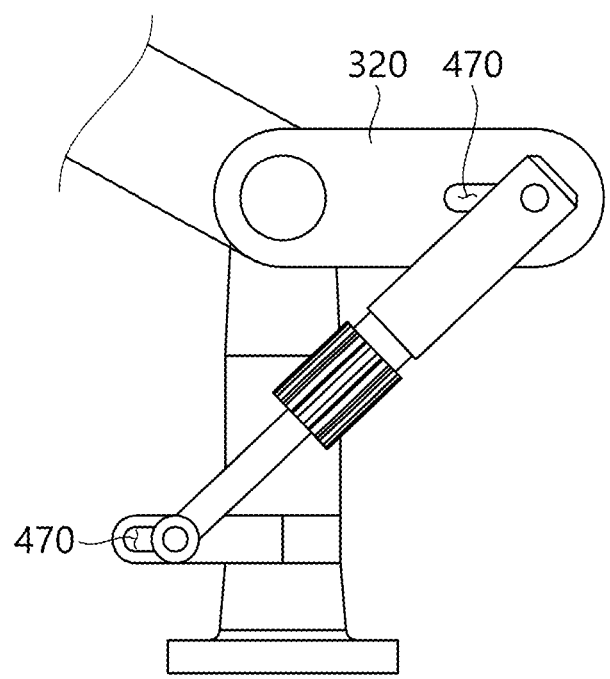
FIG. 11 is an enlarged view illustrating the elastic part according to a second embodiment.

FIG. 11 is an enlarged view illustrating the elastic part according to a second embodiment. As illustrated, the elastic part may be configured so that the position of the first hinge part 410 of the elastic part 400, the angle of the elastic part supporting part 320, and the position of the second hinge part 420 can vary. In addition, in this embodiment as well, the elastic part may be configured so that the first hinge part 410 can be connected to the first connecting area 500, and the second hinge part 420 to be connected inside the second connecting area 600. In particular, the arm supporting part 310 and the elastic part supporting part 320 may be configured to be relatively rotatable to each other. The elastic part may be configured so that the first hinge part 410 and the second hinge part 420 are fastened to a slit 470 so as to set the force required by a user to be suitable for the user's needs by changing the fastening position.

In this embodiment, the user can change the section in which the peak of the torque value occurs by adjusting each fastening position, and it becomes possible to change the varying tendency of the initial torque value. In addition, it is possible to set an appropriate torque value at the operating position.

Figure 12:
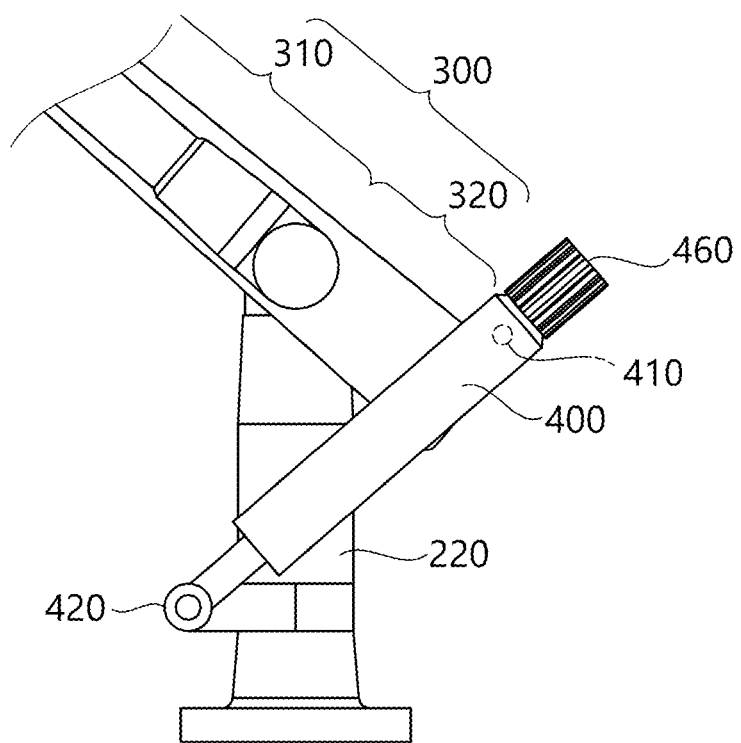
FIG. 12 is an embodiment in which the position of e elasticity adjusting part of the first embodiment is modified.

FIG. 12 is an embodiment in which the position of the elasticity adjusting part of the first embodiment is modified. As illustrated, the elasticity adjusting part 460 may be provided on the top of the elastic part 400, and it enables easy manipulation without causing any interference by the arm or mast when the user adjusts the elasticity adjusting part 460.

As described above, the spring arm for the laser treatment apparatus 100 according to the present invention can be compactly configured using a single elastic part 400, can mechanically change the maximum torque-generating angle and initial torque-generating tendency, and the support force generated in the elastic part 400 can vary according to the change in angle of the arm 200. Accordingly, the laser treatment apparatus 100 according to the present invention is effective in that the user can be freed from the requests of a sudden angle change generated by a weak support force at the initial position and a continuous force required at the use position, can easily change the laser treatment apparatus to a use position without applying an excessive force thereby being capable of reducing the user fatigue degree, and additionally, being capable of improving the accuracy of surgery.

The invention claimed is:

1. A spring arm for a laser treatment apparatus, which comprises:
   a mast comprising a first end that is mounted to a main body;

a connecting part;

an arm connected to a second end of the mast and configured to pivot in a vertical direction around the connecting part connected to the mast, wherein a laser path is provided inside the arm;

a support link comprising an arm supporting part configured to pivot around the connecting part and configured to support the arm on a first side of the connecting part;

an elastic part supporting part disposed on a second side of the connecting part that is opposite to the first side; and an elastic part having a first end connected to the elastic part supporting part, and a second end connected to the mast, wherein the elastic part comprises a first hinge part and a second hinge part, the first hinge part is connected to the elastic part supporting part, and the second hinge part is connected to the mast and configured to pivot about a first axis perpendicular to and offset from a central axis of the mast, so as to allow the elastic part to transmit a different support force to the arm depending on a vertical rotation angle of the arm.

2. The spring arm for a laser treatment apparatus of claim 1, wherein the first axis is offset from the central axis of the mast on the same side of the mast in the same horizontal direction in which the arm supporting part extends from the connecting part.

3. The spring arm for a laser treatment apparatus of claim 2, wherein the elastic part is configured to position the arm at a maximum angle without external force applied to the spring arm, and is configured to support the arm when the arm is positioned at the maximum angle.

4. The spring arm for a laser treatment apparatus of claim 3, wherein the elastic part is configured such that the amount of support provided by the elastic part decreases as the arm rotates from the maximum angle to the minimum angle.

5. The spring arm for a laser treatment apparatus of claim 2, wherein the elastic part comprises:

a housing;

a rod inserted from one side of the housing; and a spring provided inside the housing so as to transmit an elastic force between the housing and the rod.

6. The spring arm for a laser treatment apparatus of claim 5, wherein the spring is disposed between a flange at an end of the rod and a surface of an opening into which the rod is inserted, and thereby supported to be compressed when the rod is extended.

7. The spring arm for a laser treatment apparatus of claim 6, wherein the elastic part comprises an elasticity adjusting part configured to adjust the distance between the opening and the first hinge part so as to adjust the restoring force of the spring.

8. The spring arm for a laser treatment apparatus of claim 1, wherein the elastic part is configured to pivot with respect to the arm supporting part around a second axis that is offset from a central axis of the connecting part.

9. The spring arm for a laser treatment apparatus of claim 8, wherein the support link is fixed to and parallel with the arm, and the second axis is offset from a central axis of the arm.

10. The spring arm for a laser treatment apparatus of claim 1, wherein the elastic part is configured to have a length that constrains a rotation angle of the arm supporting part to a range within −0 to +90 degrees of horizontal.

11. The spring arm for a laser treatment apparatus of claim 1, wherein the mast extends in a vertical direction, and the arm, the support link, and the elastic part are configured to rotate together around a central axis of the mast.

12. The spring arm for a laser treatment apparatus of claim 11, wherein the mast is connected to the connecting part, and the support link is provided with a connecting part hole for insertion of the connecting part.

13. The spring arm for a laser treatment apparatus of claim 1, wherein a maximum angle of the arm supporting part is limited by a length of the elastic part.

* * * * *